United States Patent [19]

Chang

[11] Patent Number: 5,855,795

[45] Date of Patent: Jan. 5, 1999

[54] METHODS AND APPARATUS FOR STERILIZING PURIFIED WATER STORED IN A WATER PURIFIER

[75] Inventor: Beung-Kwon Chang, Suwon, Rep. of Korea

[73] Assignee: Samsung Electronics Co., Ltd., Suwon, Rep. of Korea

[21] Appl. No.: 749,886

[22] Filed: Nov. 18, 1996

[30] Foreign Application Priority Data

May 25, 1996 [KR] Rep. of Korea .................. 1996-17904

[51] Int. Cl.[6] .............................. B01D 17/12; A61L 2/10
[52] U.S. Cl. ......................... 210/744; 210/104; 210/138; 210/192; 210/257.1; 222/146.1; 422/24; 422/186.3
[58] Field of Search .............................. 210/86, 104, 138, 210/192, 257.1, 257.2, 259, 748, 744, 806, 184, 134; 250/435; 422/186.3, 24; 222/146.1, 189.06

[56] References Cited

U.S. PATENT DOCUMENTS

| | | | |
|---|---|---|---|
| 4,017,734 | 4/1977 | Ross | 258/435 |
| 4,801,375 | 1/1989 | Padilla | 210/257.2 |
| 4,969,991 | 11/1990 | Valadez | 210/138 |
| 5,017,284 | 5/1991 | Miler et al. | 210/257.2 |
| 5,064,097 | 11/1991 | Brog et al. | 222/146.1 |
| 5,582,717 | 12/1996 | Di Santo | 210/192 |

FOREIGN PATENT DOCUMENTS

| | | | |
|---|---|---|---|
| 3181389 | 8/1991 | Japan | 210/138 |
| 1445799 | 8/1976 | United Kingdom | 210/138 |

*Primary Examiner*—Joseph W. Drodge
*Attorney, Agent, or Firm*—Burns, Doane, Swecker & Mathis, L.L.P.

[57] ABSTRACT

A water purifier includes filters for purifying tap water, a storage tank for storing the purified water, and hot and cold water tanks for respectively heating and cooling water received from the storage tank. Water is dispensed from the hot and cold water tanks. An ultraviolet lamp is provided for sterilizing water in the storage tank. A controller controls a valve for supplying tap water to the filters. The controller closes the valve when water in the storage tank reaches a first reference level and opens the valve when the water level descends to a second reference level. The controller keeps the lamp deactivated while the valve is open, and activates the lamp at periodic intervals during a time when the water level remains above a third reference level.

7 Claims, 5 Drawing Sheets

METHODS AND APPARATUS FOR STERILIZING PURIFIED WATER STORED IN A WATER PURIFIER

FIELD OF THE INVENTION

The present invention relates to a hot and cold water purifier for removing harmful pollution materials contained in potable water such as faucet water and the like to thereby purify the water, and more particularly to a sterilization apparatus of hot and cold water purifier and method thereof for sterilizing the purified water effectively.

DESCRIPTION OF THE PRIOR ART

Generally, hot and cold water purifier serves to remove harmful cancer-causing materials contained in potable water such as faucet water and the like to thereby supply purified water, and according to purifying method thereof, the water purifier can be classed into a naturally-filtering type, a directly-connected type, an ion exchange resin type and an inverted osmotic pressure type.

Among those type, the water purifier by the inverted osmotic pressure method serves to apply pressure to the potable water to force it through a membrane which is an artificial osmotic membrane (an inverted osmotic filter), thereby performing the water purifying.

The water purifier by the inverted osmotic pressure method is widely used in the most sophisticated scientific industries for cleaning hyper precision electronic parts or in medical fields in that it can separately remove heavy metals, bacteria, cancer-causing materials and the like, and at the same time, it can supply only the purified water containing clean water and dissolved oxygen.

This type water purifier can separately remove heavy metals, bacteria, cancer-causing materials and the like contained in the potable water through multiple filters, and also the purified water is stored in cold water and hot water tanks separately and thereafter the purified water is cooled or heated to reach predetermined temperature degrees by user.

Meanwhile, an ultraviolet lamp installed in the water tanks is driven to emit ultraviolet rays continuously while purifying operation so as to remove the harmful bacillus.

The ultraviolet lamp keeps to continuously emit the ultraviolet rays for a predetermined time at the beginning of purifying operation, but it is not driven when a water level of the water tank is a level not necessary more purifying operation and when the purified water is discharged outside.

However, there is a problem in the conventional water purifier in that the ultraviolet lamp is driven to emit the ultraviolet rays continuously not only when an initial purifying operation is performed but also when the purified water reaches full level from middle level thereby causing the ultraviolet lamp to shorten in it's life and causing a bad smell to give out due to generation of ozone.

SUMMARY OF THE INVENTION

Accordingly, the present invention has been disclosed to solve the aforementioned problem and it is an object of the present invention to provide a sterilization apparatus of hot and cold water purifier and method thereof by which ultraviolet lamp is driven at every 1 to 4 hours so as to prevent the generation of OZONE($O_3$), and to increase a sterilization power, and to lengthen the lamp's life by reduction of lamp operating time.

In accordance with the object of the present invention, in a hot and cold water purifier in which a water tank, a cold water tank and a hot water tank are provided to supply cold water and hot water stored through a plurality of filters a sterilization apparatus of a water purifier comprising:

water level detecting means for detecting a water level of the water tank;

control means for controlling an ultraviolet lamp on the basis of time counted according to a water level signal output from the water level detecting means; and lamp driving means for driving the ultraviolet lamp so as to emit ultraviolet rays to thereby remove harmful vacillus in the water tank.

In accordance with the present invention, there is provided a control method of a hot and cold water purifier, the method comprising the steps of:

purifying potable water by means of a sedimentation filter, a pre-processing filter, a membrane and a post-processing filter;

detecting a water level of the water tank;

discriminating whether or not an ultraviolet lamp has to be driven on the basis of time counted according to a water level of the water tank; and sterilizating the purified water stored in the water tank by driving the ultraviolet lamp in case of a ultraviolet lamp operating times.

BRIEF DESCRIPTION OF THE DRAWINGS

For fuller understanding of the nature and objects of the invention, reference should be made to the following detailed description taken in conjunction with the accompanying drawings in which.

DETAILED DESCRIPTION OF THE INVENTION

The embodiment of the present invention will now be described in detail with reference to the accompanying drawings.

Figure 2:
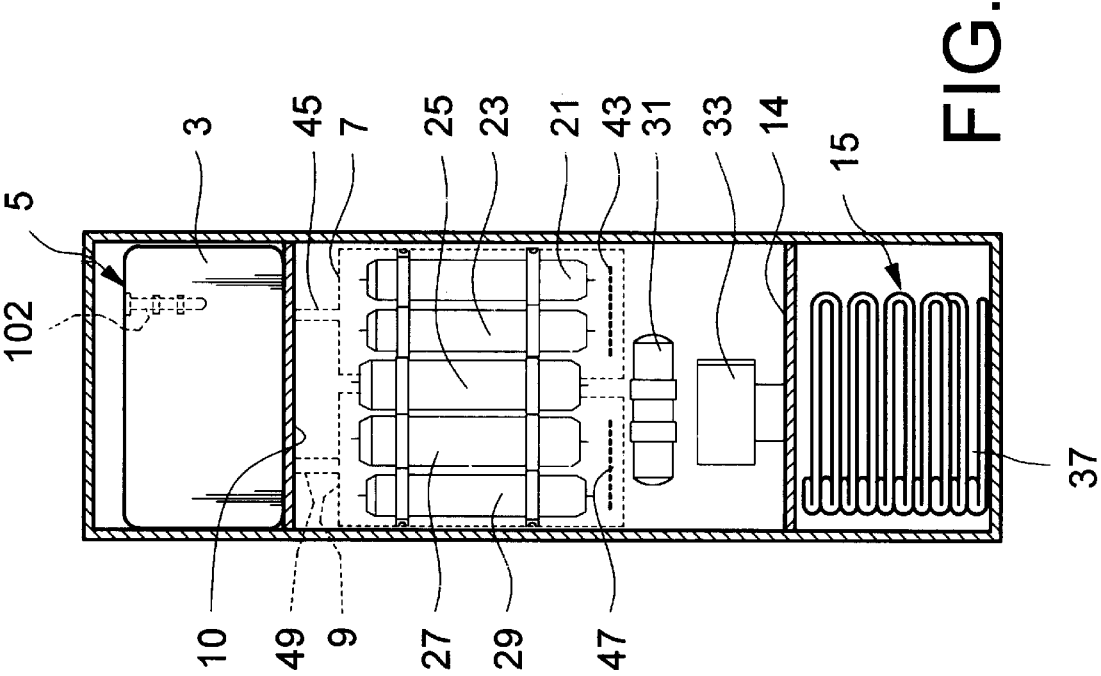
FIG. 2 is a sectional view taken along A—A line in FIG. 1.
Figure 1:
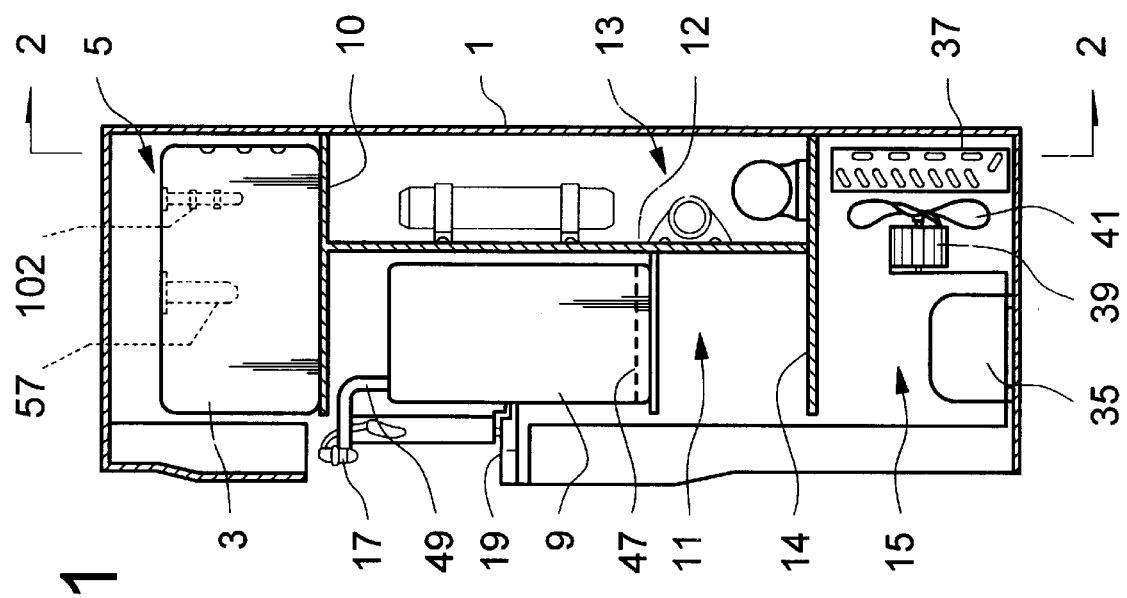
FIG. 1 is a longitudinal sectional view of a hot and cold water purifier according to the present invention.

As shown in FIGS. 1 and 2, a hot and cold water purifier comprising:

a water purifying compartment 5 arranged at the upper portion of a body 1 of the purifier for accomodating the water tank 3;

a cooling and hot water compartment 11 arranged at the lower portion of the water purifying compartment 5 for accomodating a cold water tank 7 and a hot water tank 9;

filtering compartment 13 arranged at the lower portion of the cooling and hot water compartment 11 for accomodating a plurality of filters to remove the harmful bacillus, materials contained in the potable water such as faucet water and the like to thereby supply purified water, machine compartment 15 for accomodating refrigerating means such as, a compressor 35, a fan motor 39 and a condenser 37 to cool the purified water in the cooling water tank 7; and water discharge lever 17 arranged at the front side of the body 1 of the water purifier to be discharged the purified water in the cold and hot water tanks 7 and 9.

The water tank 3 is arranged at the inner side thereof with an ultraviolet lamp 57 for sterilizing harmful bacillus contained in the purified water therein by emitting ultraviolet rays, and the float sensor 102 for detecting the water level of the purified water tank 3.

The filtering compartment 13 is arranged at the inner side thereof with a sedimentation filter 21 for removing floating substances, rust and the like contained in potable water such as faucet water and with a pre-processing filter 23 for removing organic chemical materials containing various harmful substances such as chlorine substance and the like contained in potable water which has passed through the sedimentation filter 21.

Furthermore, the filtering compartment 13 is arranged at the inner side thereof with a membrane 25 for removing various heavy metals, cancer-causing materials, bacteria and the like contained in the potable water which has passed through the pre-processing filter 23, and with a post-processing filter 27 for removing odor substance such as harmful gas contained in the potable water which has passed the post-processing filter 23.

Further, the sedimentation filter 21, the pre-processing filter 23, the membrane 25 and post-processing filter 27 are arranged at lower portion thereof with a pressuring pump 33 in order to increase to a predetermined pressure of the potable water infused into the membrane 25, so that the potable water infused into the membrance 25 through the pre-processing filter 23 can be purified by the inverted osmotic pressure at the membrane 25 with the predetermined pressure.

Meanwhile, the machine compartment 15 is arranged at an inner portion thereof with the compressor 35 for compressing a refrigerant of low temperature and pressure, thereby causing the refrigerant to be high temperature and pressure and the condenser 37, where the gaseous refrigerant of high temperature and pressure which has been compressed by the compressor 35 carries out a heat-exchange with ambient air in accordance with the natural or forced convection phenomenon, so that it is forcedly cooled to have a liquid phase under low temperature and high pressure, and a rotating fan 41 for circulating air around the compressor 35 and the condenser 37 so as to liquefying the refrigerant which has passed the condenser 37 and to cool the compressor 35.

At the inner portion of the cool water tank 7, an evaporator 43 is arranged so as to evaporate a refrigerant flowing through a evaporation tube 43 to cool the pure water in the cool water tank 7 by way of latent heat of the refrigerant. The cold water tank 7 is connected with a conduit 45 for guiding the cool water being discharged by the manipulating of the discharge a level 17.

At the inner portion of the hot water tank 9, a heater 47 for heating the purified water in the hot water tank 9 is installed. The hot water tank 9 is connected with a conduit 49 for guiding the hot water being discharged by the manipulating of the discharge level 17.

Meanwhile, the inside of the body 1 is partitioned into four compartments by means of members 10, 12 and 14 namely, the water purifying compartment 5, the hot and cool water compartment 11, the filtering compartment 13 and the machine compartment 15.

Unexplained reference number 19 is water spout member installed below the lever 17 for receiving water dropping water according to operating of the lever 17.

Figure 3:
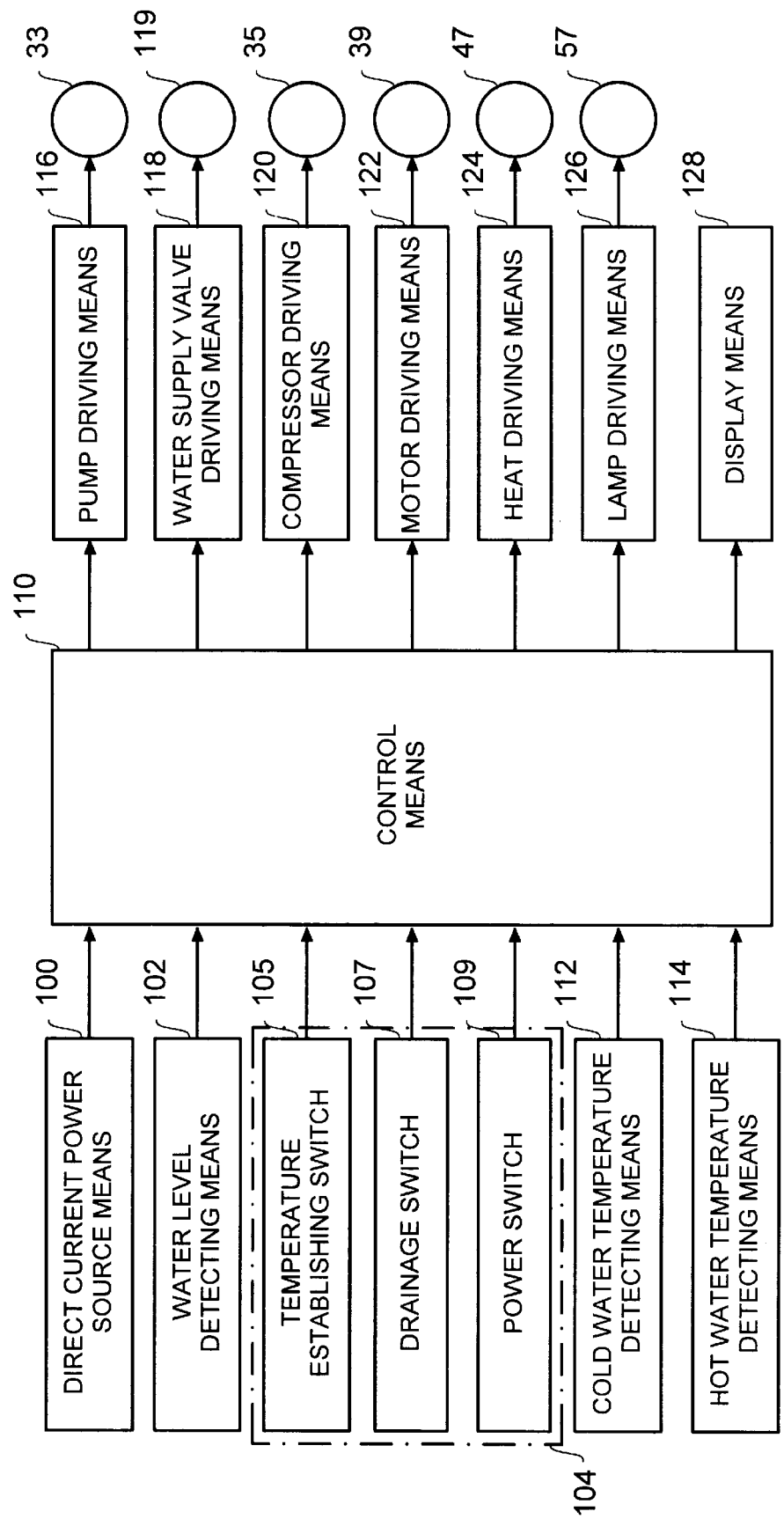
FIG. 3 is a block diagram illustrating a sterilization apparatus of a hot and cold water purifier according to the present invention.

As illustrated in FIG. 3, direct current (DC) power source means 100 serves to receive a power source voltage of commercial alternating current power source supplied from an alternating current (AC) power source input terminal (not shown) to thereby convert same to a predetermined direct current (DC) voltage necessary for the operation of the water purifier.

Water level detecting means 102 is water level sensor for detecting the water level of the water tank 3. The water level detecting means 102 is a float sensor.

Key signal input means 104 serves to establish the temperature of cold and hot water stored in the cold water and hot water tanks 7 and 9. The key signal input means 104 comprises a temperature establishing switch 105, and a drainage switch 107 to drainage the purified water stored in the tanks 3, 7 and 9, and a power switch 109 for controlling the supply of electric power source to the water purifier.

Control means 110 is a microcomputer for receiving the DC voltage output from the DC power source means 100 to initialize the operation of the water purifier and for receiving key signal from the key input means 104 to thereby control overall water purifying operations. The control means 110 controls the ultraviolet lamp 57 at every 1 to 4 hours on the basis of time counted according to water level signal detected by the water level detecting means 102. The time may be counted by a timer previously provided in the control means 110.

Furthermore, cold water temperature detecting means 112 serves to detect the temperature Tc of cold water stored in the cold water tank 7, thereby outputting the detected temperature to the control means 110.

Hot water temperature detecting means 114 serves to detect the temperature Th of hot water stored in the hot water tank 9, thereby outputting the detected temperature to the control means 110.

Furthermore, pump driving means 116 serves to receive a control signal generated from the control means 110 according to the water level of the water tank 3 detected by the water level detecting means 102 to controllably drive the pressurizing pump 33 so that the potable water can be supplied to the tank 3.

Water supply valve driving means 118 is adapted to receive a control signal generated from the control means 110 according to the water level of the water tank 3 detected by the water level detecting means 102 to controllably drive the water supply valve 119, so that supply or interdiction of the potable water supplied through a water supply tube from the faucet can be controlled.

Compressor driving means 120 is adapted to receive a control signal generated from the control means 110 according to the difference between a predetermined cold water temperature (Tcs) fixed by temperature establishing switch 105 and a cold water temperature (Tc) detected by cool water temperature detecting means 112 to controllably drive the compressor 35 so that the purified water in cold water tank 7 can be cooled.

Motor driving means 122 is adapted to receive a control signal generated from the control means 110 according to the difference between the predetermined temperature (Tcs) fixed by temperature establishing switch 105 and the cold water temperature (Tc) detected by temperature detecting means 112 to controllably drive the fan motor 39, so that the heat exchanged by the condenser 37 is discharged outside, simultaneously to control a numbers rotation of fan motor 39, thereby controlling fan 41, so that the purifier water in cold water tank 7 can be cooled.

Heater driving means 124 is adapted to receive a control signal generated from the control means 110 according to the difference between a predetermined hot water temperature Ths fixed by temperature establishing switch 105 situated in key input means 104 and a hot water temperature Th detected by hot water temperature detecting means 114 to controllably drive the heater 47 so that purified water in hot water tank 9 can be heated.

Lamp driving means 126 is adapted to receive a control signal generated from the control means 110 to controllably drive the ultraviolet lamp 57 so that the purified water in the water tank 3 is being purified by ultraviolet rays.

Display means 128 serves to display predetermined cool and hot water temperature Tcs and Ths established by the temperature establishing switch 105 of the key signal input means 104 and to display the cold water temperature Tc detected by cold water temperature detecting means 112 and to display the hot water temperature Th detected by the hot water temperature detecting means 114.

Now, operational effect of purification and control method in the hot and cold water purifier thus constructed will be described.

Figure 4A:
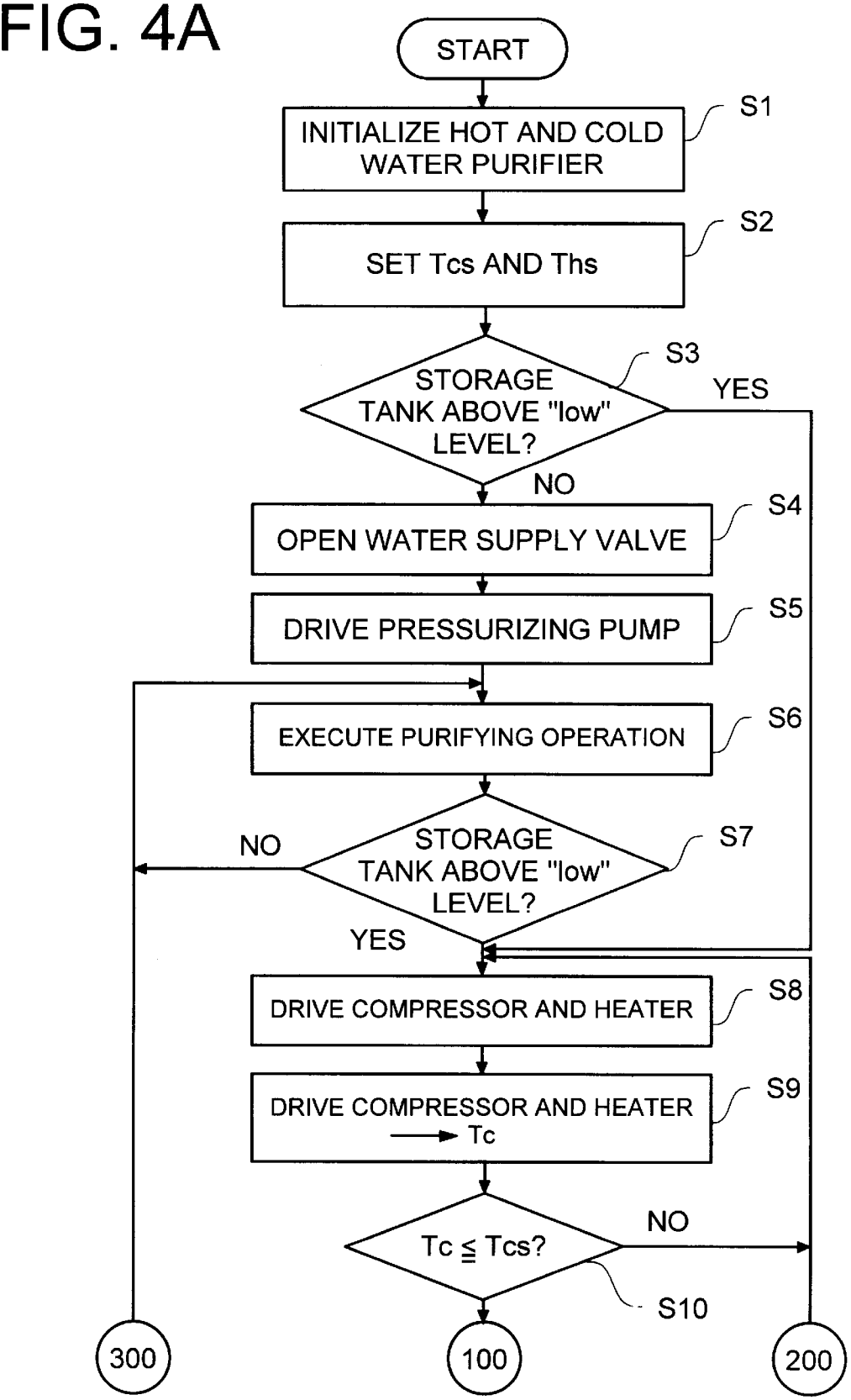
FIGS. 4A to 4C are flow charts respectively illustrating the sequence of a method for controlling the sterilizing operation of the hot and cold water purifier.
Figure 4B:
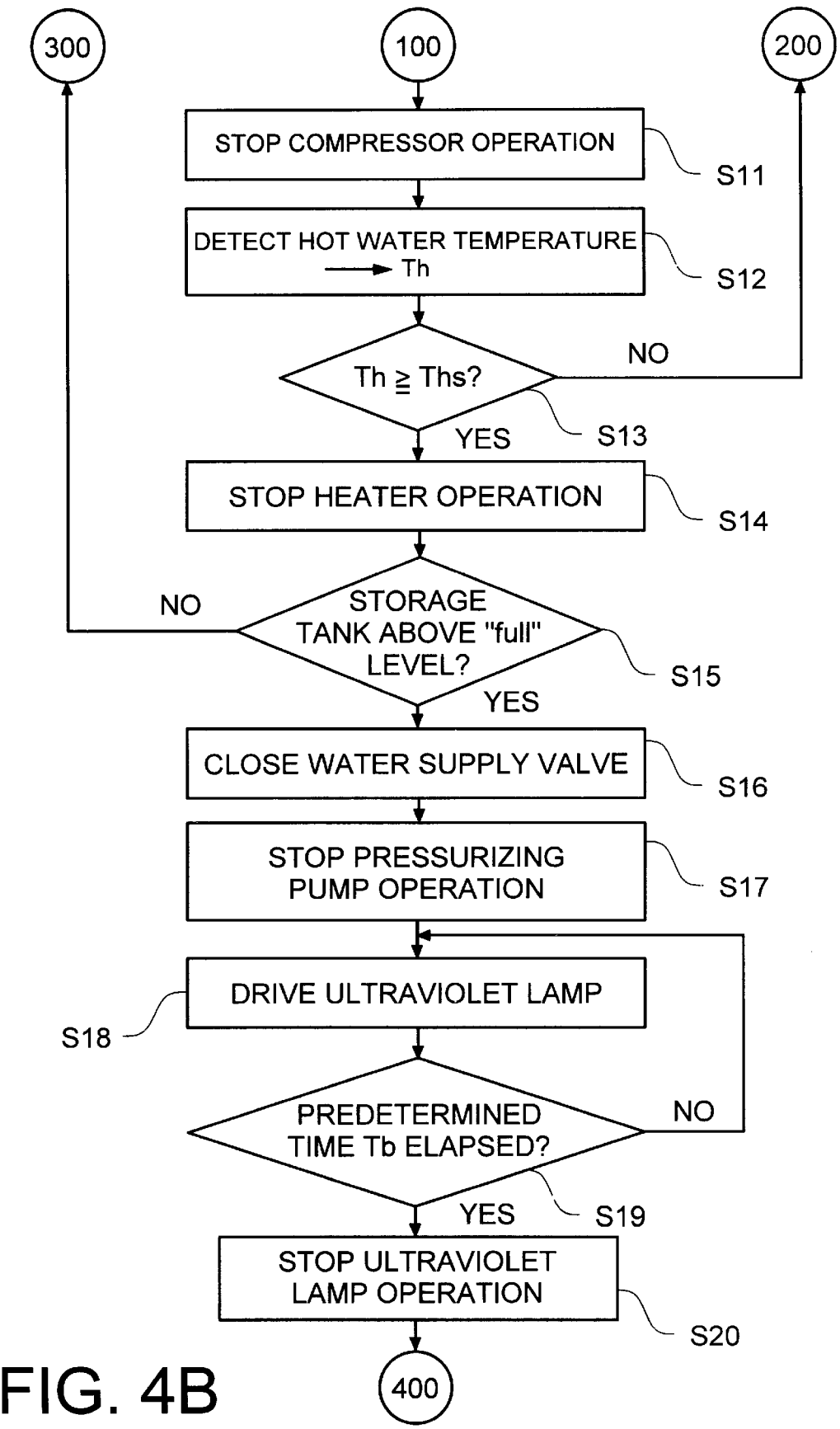
Figure 4C:
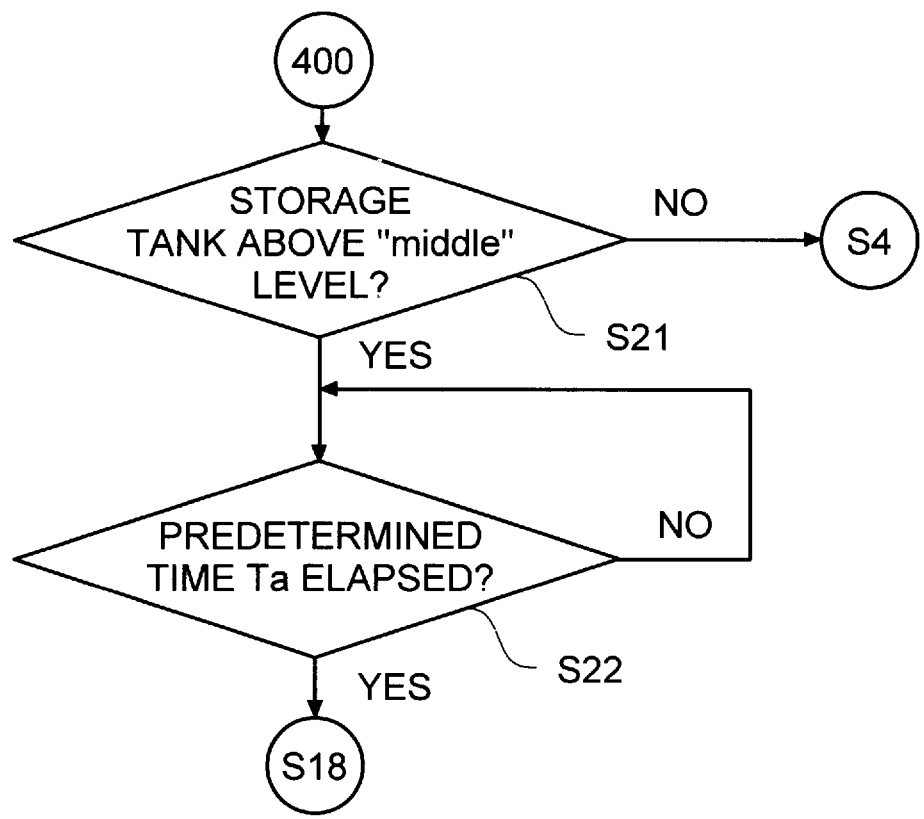

FIGS. 4A through 4C are flow chart for illustrating operational procedure of purification in hot and cool water purifier, where reference symbols S indicate steps.

First of all, when a power supply is applied to the hot and cold water purifier, the direct current power source means 100 serves to convert a power source voltage of the commercial alternating current power source supplied from the alternating current power source input terminal (not shown) to a predetermined direct current voltage necessary for driving the water purifier, to thereby generating same to respective driving circuits and the control means 110.

Accordingly, at step S1, the direct current voltage output from the direct current power source means 100 is received at the control means 110 to thereby initialize the hot and cold water purifier. At step S2, the user manipulates the cold water or hot water selection switches not shown to select cold water or hot water, and manipulates the temperature establishing switch 105 to be established cold water temperature Tcs and hot water temperature Ths.

At this time, the display means 128 serves to display the established (predetermined) cold and hot water temperatures Tcs and Ths according to the control signal generated from the control means 110.

Subsequently, at step S3, as soon as the power switch is turned on, the water level detecting means 102 detects the water level of the tank 3, i.e., the water quantity of the tank 3, to thereby output a water level data detected therefrom to the control means 110.

Accordingly, the control means 110 discriminates whether the water level of the tank 3 detected by the water level detecting means 102 is above "low" level. The level "low" means about 10% if the level "full" is 100%.

Meanwhile, as a result of the discrimination at step S3, when the water level of the tank 3 is not above low level (in case of NO), the control means 110 outputs a control signal at step 4 to the water supply valve driving means 118 for opening the water supply valve 119, so that water purifying operation can be executed for supplying the purified water into the tank 3.

Accordingly, the water supply valve driving means 118 supplies a power source voltage to the water supply valve 119 under the control of the control means 110 thereby opening the water supply valve 119.

When the water valve 119 is opened, the portable water such as the faucet water starts to be inflowed into the water supply tube 119 and the control means 110 outputs to the pump driving means 116 at step S5 a control signal for driving the pressurizing pump 33, so that the potable water being supplied into the water supply tube and infused into the membrane 25 can be raised in pressure to a predetermined level.

Accordingly, the pump driving means 116 receives the control signal generated from the control means 110 to thereby supply the power source voltage applied to the pressurizing pump 33, so that the pressurizing pump 33 can be driven.

When the pressurizing pump 33 is driven, the potable water supplied into the water tube (not shown) from the faucet according to the opening of the water supply valve 119 is removed of the floating matters and rust, and the potable water which has passed the sedimentation filter 21 is infused into the pre-processing filter 23 to thereby be removed of the various harmful organic chemical materials such as the chloric substance and the like at step S6.

The potable water which has passed the pre-processing filter 23 is infused into the membrane 25 according to the driving of the pressurizing pump 33. The potable water which has infused into the membrane 25 passes the multiple membrane filters to thereby be removed of various harmful chemical materials, cancer-causing substance and a bacillus, i.e. bacteria.

The potable water which has passed the membrane 25 passes in turn through the post-processing filter 27 to thereby be removed of the odors such as the poisonus gas and the like, and then, the water purifying operation, where the purified water is supplied into the pure water storage tank 3, and cold water tank 7 and hot water tank 9 in order through the water supply hole (not shown) is executed.

Subsequently, at step S7, the water level detecting means 102 detects the water level of the tank 3 i.e., the purified water quantity supplied to the tank 3 through the water supply hole (not shown) during the water purifying operation at step S6 thereby to output a water level data detected therefrom to the control means 110.

Accordingly, the control means 110 discriminates whether the water level of the tank 3 detected by the water level detecting means 162 is above "low".

As a result of discrimination at step S7, when the water level of the tank 3 is "low" (in case of NO), flow returns to step S6 and performs the water purifying operation, and repeatedly executes the operations subsequent to step S6.

Meanwhile, as a result of the discrimination at step S7, when the water level of the tank 3 is above "low" (in case of YES), flow advances to step S8, where the control means 110 outputs to the compressor driving means 120 and heater driving means 124 simultaneously for driving compressor 35 and the heater 47 and also outputs to the motor driving means 122 for driving the fan motor 39.

Accordingly, the compressor driving means 120 drives the compressor 35 and the heater driving means 124 drives the heater 47 and the motor driving means 122 drives the fan motor 39 according to the control signals generated from the control means 110.

When the compressor 35 and the fan motor 39 are driven, the gaseous refrigerant of high temperature and pressure which has been compressor 35, while passing through the condenser 87, carries out a heat-exchange with ambient air in accordance with the natural of forced convection phenomenon, so that it is forcedly cooled to have a liquid phase under low temperature and high pressure.

The low temperature and high pressure refrigerant passed through the condensor 37 is reduced its pressure by a capillary tube not shown to thereafter be infused into the evaporator tube 43.

Successively, while passing through the evaporator 43 which is constituted a plurality of pipes, the refrigerant of low temperature and pressure carries out a heat exchange with the purified water stored in the tank 7, and then the cooled refrigerant is again infused into the compressor 35 thereby repeatedly performing the refrigerant cycle.

Accordingly, the purified water stored in the tank 7 is cooled and to thereby become a cold pure water according to a repeated refrigerating cycle.

Meanwhile, when the heater 47 is driven, purified water in the hot water tank 9 is heated to thereby be heated according to the driving of heater 47.

Operation of purifying is executed continuously until the water level of the tank 3 reaches full level even when purified water in the cold water tank 7 and the hot water tank 9 is cooled and heated.

At this time, at the step S9, the cold water temperature detecting means 112 detects the temperature Tc of cold water decreasing according to a repeated refrigerating cycle in the cold water tank 7 to thereby output to the control means 110 and the display means 120 displays the temperature Tc of cold water detected by the cold water temperature detecting means 112 according to the control signal of the control means 110.

Subsequently, at the step S10, the control means 110 discriminates whether the temperature of cold water Tc detected by a cold water temperature detecting means 112 is below the predetermined temperature Tcs established by the temperature establishing switch 105.

As the result of discrimination at the step S10 when the temperature Tc of cold water is not below the predetermined temperature Tcs (in case of NO), flow returns to step S8 and repeatedly executes the operations subsequent to step S8 because purified water in the cool water tank 7 must be cooled continuously.

On the other hand, as the result of the discrimination at step S10 when the temperature Tc of cold water is below the predetermined temperature Tcs (in case of yes) flow advances to the step S11.

At the step S11, the compressor driving means 120 and the motor driving means 122 serve to stop the driving the compressor 35 and the fan motor 39 respective because it is unnecessary to cool the purified water in the cold water tank 7 any more.

Subsequently, at the step S12, the hot water temperature detecting means 114 detects the hot water temperature Th in the hot water tank 9 rising caused by operations of the heater 47 to thereby output to the control means 110 and the display means 128 displays the hot water temperature Th detected by the hot water temperature detecting means 114. At the step S13, the control means 110 discriminates whether the hot water temperature Th detected by the hot water temperature detecting means 114 is above the predetermined temperature Ths established by the temperature established switch 105.

As the result of the discrimination at step S13 when the hot water temperature Th is not above the predetermined temperature Ths (in case of NO), flow returns to the step S8 and executes repeatedly operations subsequent to the step S8.

As the result of discrimination of the step S13, when the hot water temperatures Th is above the predetermined temperatures Ths (in case of YES), flow advances to the step S14.

At the step S14, the heater driving means 124 stops driving the heater 47 according to the control signal generated from the control means 110.

Subsequently, at the step S15, the water level detecting means 102 detects the water level of the tank 3 changed by inflow of water into the tank 3 according to the purifying operations at the step S6 to thereby discriminate whether the water level is above "full" level.

As the result of discrimination at the step S15, when the water level of tank 3 is not above "full" level (in case of NO), flow returns to the step S6 and performs purifying operations to thereby executes repeatedly operations subsequent to the step S6.

Meanwhile, as the result of the discrimination at the step S15, when the water level of the tank 3 is above full level (in case of YES), flow advances the step S16 and the control means 110 outputs the control signal to the water supply valve driving means 118 to close the water supply valve 119 because inflow of purified water into the tank 3 must be stopped.

Therefore, the water supply driving means 118 cuts off the power supply source being supplied to the water supply valve 119 according to the control signal generated from the control means 110.

At this time, at the step S17, the pump driving means 116 cuts off the power supply source being supplied to the pressurizing pump 33 according to the control signal generated from the control means 110.

When the water supply valve 119 is closed, and the pressurizing pump 33 stops driving the supply of the potable water supplied from the faucet is cut off to thereby stop the purifying operations.

Successively, when the water level of the tank 3 is full level at the step S18, the control means 110 outputs the control signal to the lamp driving means 126 for driving the ultraviolet lamp 57.

Therefore, the lamp driving means 126 drives the ultraviolet lamp 57 according to the control signal generated from the control means 110 to thereby remove the harmful bacillus, i.e., bacteria contained in purified water by emitting ultraviolet rays.

At this time, a discrimination is made at step S19 as to whether operation time of the ultraviolet lamp 57 counted at the timer previously stored at the control means 110 has passed a predetermined time (Tb: Time to remove the harmful bacillus contained in purified water, approximately one to five minutes) and when the operation time of the ultraviolet lamp 57 has not passed the predetermined time Th (in case of NO), flow returns to the step S18, where lamp driving means 126 continues to drive the ultraviolet lamp 57 until operation time of the ultraviolet lamp 57 has passed the predetermined time Tb according to the control signal generated from the control means 110 and execute the operations repeatedly subsequent to the step S18.

As a result of discrimination of the step S19 when the operation time of the ultraviolet lamp 57 has passed the predetermined time Tb (in case of YES), it is discriminated that the harmful bacillus such as bacteria, and the like are removed from the water purifying tank 3 and lamp driving means 126 serves to stop driving the ultraviolet lamp 57 according to the control signal generated from the control means 110.

Subsequently, at the step S21, the water level detecting means 102 detects the water level of the tank 3 and a water level detected therefrom is outputted to the control means 110.

Successively the control means 110 discriminates whether the water level of the tank 3 detected by the water level detecting means 110 is above "middle" level. When the water level is not above "middle" level (in case of NO), flow returns to the step S4 and performs purifying operations to thereby execute repeatedly operations subsequent to the step S4.

As a result of discrimination of the step S21, when the water level of the tank 3 is above "middle" level (in case of YES) flow advances to the step 22.

At the step S22, the control means 110 stops purifying operations and discriminates whether time counted at the timer stored at the control means 110 exceeds the predetermined time limit (Ta: times that sterilizing power is lasting, approximetely one to four hours).

When times has not been passed the predetermined times Ta (in case of NO), flow returns to the step S22 again and executes repeatedly operations subsequent to the step S22.

As a result of discrimination at step 22, when time counted at the time stored at the control means 110 has been passed the predetermined time Ta (in case of YES), flow returns to the step S18 and the control means 110 drives the ultraviolet lamp 57 to thereby emit the ultraviolet rays to remove the harmful bacillus contained in purified water of the tank 3 and executes repeatedly operations subsequent to the step S18.

Meanwhile, when the water level of the tank 3 is "middle" level if drainage operations is accomplished when the water level is "middle" or if purified water is flowed out continuously, the operations of the ultraviolet lamp 57 comes to be stopped.

Further, as the result of discrimination of the step S3, when the water level of the tank 3 is above "low" level (in case of YES), flow advances to the step S8 to cool and to heat the purified water stored separately in the cold water tank 7 and hot water tank 9.

As apparent from above, a sterilization apparatus of hot and cold water purifier and method thereof according to the present invention when the water level of the pure water storage tank is above "middle" or "full" the lamp driving means serves to drive the ultraviolet lamp at the 1 to 4 hours intervals according to the control signal generated from the control means thereby preventing production of ozone and improving sterilization power, and reducing the lamp operating time, it thus certain that the life of the lamp can be prolonged.

Having described specific preferred embodiment of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method of operating a water purifier, comprising the steps of:

A) passing water through a filter arrangement for purifying the water, and storing the purified water in a storage tank having an outlet for discharging purified water;

B) terminating step A when a water level detecting device detects that a water level in the storage tank reaches a first reference level;

C) resuming step A when the water level detecting device detects that the water level in the storage tank has descended to a second reference level which is lower than the first reference level;

D) activating an ultraviolet lamp to sterilize water in the storage tank for a predetermined time period in response to the water level detecting device detecting that a rising water level in the storage tank exceeds the first reference level, whereby the ultraviolet lamp is always activated immediately after a rising water level is detected as exceeding the first reference level; and E) keeping the ultraviolet lamp deactivated during steps A and C.

2. The method according to claim 1 wherein after step D, the ultraviolet lamp is again activated in response to the water level in the tank exceeding a third reference level over a time interval of in the range of 1 to 4 hours.

3. The method according to claim 2 wherein step D comprises activating the ultraviolet lamp for a period of in the range of 1 to 5 minutes.

4. The method according to claim 1 wherein the predetermined time period in step D is in the range of 1 to 5 minutes.

5. The method according to claim 1, further including the step of supplying purified water from the storage tank to hot and cold water tanks to be heated and cooled, respectively.

6. A water purifier, comprising:

a filter arrangement adapted to receive and purify water;

a storage tank for receiving purified water from the filter arrangement, the storage tank having a water outlet for discharging purified water and a detector for detecting a level of water in the storage tank;

an ultraviolet lamp for sterilizing water in the storage tank;

a valve for selectively allowing fluid communication between the filter arrangement with a source of water to allow a flow of water through the filter arrangement;

a controller connected to the detector and to the valve for closing the valve for terminating the flow of water through the filter arrangement in response to a signal from the detector that a rising water level in the storage tank exceeds a first reference level, the controller connected to the ultraviolet lamp and including a timer for activating the ultraviolet lamp for a predetermined time period in response to said signal from the water detector whereby the ultraviolet lamp is always activated immediately after a rising water level exceeds the first reference level, the controller being operable for opening the valve to admit a flow of water through the filter arrangement when the water level in the tank descends below a second reference level which is lower than the first reference level.

7. The water purifier according to claim 6, further including hot and cold water tanks for receiving purified water from the storage tank and for respectively heating and cooling the received water.

\* \* \* \* \*